(12) United States Patent
Wallace et al.

(10) Patent No.: US 7,242,134 B2
(45) Date of Patent: Jul. 10, 2007

(54) ELECTROMECHANICAL ACTUATOR AND METHODS OF PROVIDING SAME

(75) Inventors: Gordon G. Wallace, Gwynneville (AU); Geoffrey M. Spinks, Balgownie (AU); Dezhi Zhou, Corrimal East (AU)

(73) Assignee: University of Wollongong, New South Wales (AU)

( * ) Notice: Subject to any disclaimer, the term of this patent is extended or adjusted under 35 U.S.C. 154(b) by 5 days.

(21) Appl. No.: 10/496,262

(22) PCT Filed: Nov. 25, 2002

(86) PCT No.: PCT/AU02/16080

§ 371 (c)(1),
(2), (4) Date: Sep. 7, 2004

(87) PCT Pub. No.: WO03/043541

PCT Pub. Date: May 30, 2003

(65) Prior Publication Data

US 2005/0006989 A1    Jan. 13, 2005

(30) Foreign Application Priority Data

Nov. 23, 2001 (AU) .................................. PR9071

(51) Int. Cl.
*H01L 41/08* (2006.01)
(52) U.S. Cl. ...................... 310/363; 310/800
(58) Field of Classification Search ............... 310/311, 310/328, 330–332, 363, 364, 800
See application file for complete search history.

(56) References Cited

U.S. PATENT DOCUMENTS

| | | | |
|---|---|---|---|
| 3,817,193 A | 6/1974 | Frankel et al. | |
| 3,910,775 A | 10/1975 | Jackman | |
| 4,017,395 A | 4/1977 | Davis | |
| 4,423,768 A * | 1/1984 | Edelman et al. | 165/84 |
| 4,670,074 A * | 6/1987 | Broussoux et al. | 156/198 |
| 4,786,837 A * | 11/1988 | Kalnin et al. | 310/364 |
| 5,410,210 A * | 4/1995 | Sato et al. | 310/363 |
| 5,620,594 A | 4/1997 | Smith et al. | |
| 6,545,384 B1 * | 4/2003 | Pelrine et al. | 310/309 |
| 6,911,764 B2 * | 6/2005 | Pelrine et al. | 310/328 |
| 6,936,955 B1 * | 8/2005 | Smela et al. | 310/363 |
| 6,982,514 B1 * | 1/2006 | Lu et al. | 310/300 |
| 7,038,357 B2 * | 5/2006 | Goldenberg et al. | 310/328 |

FOREIGN PATENT DOCUMENTS

| | | |
|---|---|---|
| ES | 2062930 | 12/1994 |
| JP | 2000-083389 | 3/2000 |
| JP | 2000-133854 | 5/2000 |
| WO | WO 97/36366 | 10/1997 |
| WO | WO 99/17929 | 4/1999 |
| WO | WO 01/06575 | 1/2001 |

OTHER PUBLICATIONS

Arbizzani et al., Lithium/polymer/polymer solid-state rechargeable batteries, Journal of Power Sources, 1993, pp. 453-460.

(Continued)

*Primary Examiner*—Mark Budd
(74) *Attorney, Agent, or Firm*—Marshall, Gerstein & Borun LLP

(57) ABSTRACT

An electromechanical actuator comprising an inherently conducting polymer and a conductor for conducing voltage along the polymer from a first end region thereof. The conductor is adapted for axially extending and contracting with axial expansion and contraction of the polymer. In one form, the conductor is in the form of a helix embedded in the polymer and extends along substantially the entire length of the polymer. Also disclosed is a method for manufacture of the electromechanical actuator.

26 Claims, 8 Drawing Sheets

OTHER PUBLICATIONS

Baughman, Conducting polymer artificial muscles, Synthetic Materials, 1996, pp. 339-353.

Gandhi et al., Mechanism of electromechanical actuation is polypyrrole, Synthetic Materials, 1995, pp. 247-256.

Hashmi et al., Conducting Polymer-based Electrochemical Redox Supercapacitors Using Proton and Lithium Ion Conducting Polymer Electrolytes, Polymer International, 1998, pp. 28-33.

Lewis et al., Development of an all-polymer, axial force electrochemical actuator, Synthetic Materials, 19991, pp. 1317-1318.

Lewis et al., Evaluation of Solid Polymer Electrolytes for use in Conducting Polymer/ Nanotube Actuators, Smart Structures and Materials 2000: Electroactive Polymer Actuators and Devices, 2000, pp. 351-357.

Murray et al., Electrochemical induced ductile-brittle transition in tosylate-doped (pTS) polypyrrole, Synthetic Materials, 1998, pp. 117-121.

Spinks et al., Strain Response from Polypyrrole Actuators under Load, Advanced Functional Materials, Jun. 2002, vol. 12, No. 6-7, pp. 437-440.

Yamada et al., A Solid-State Electrochemical Device Using Poly(pyrrole) as Micro-actuator, Jpn. J. Appl. Phys., Oct. 1998, vol. 37, Part 1, No. 10, pp. 5798-5799.

* cited by examiner

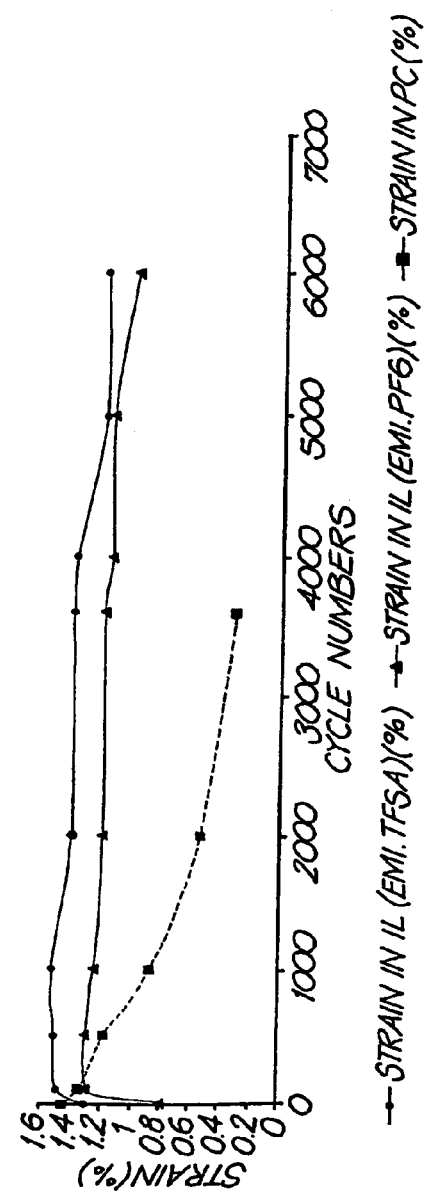
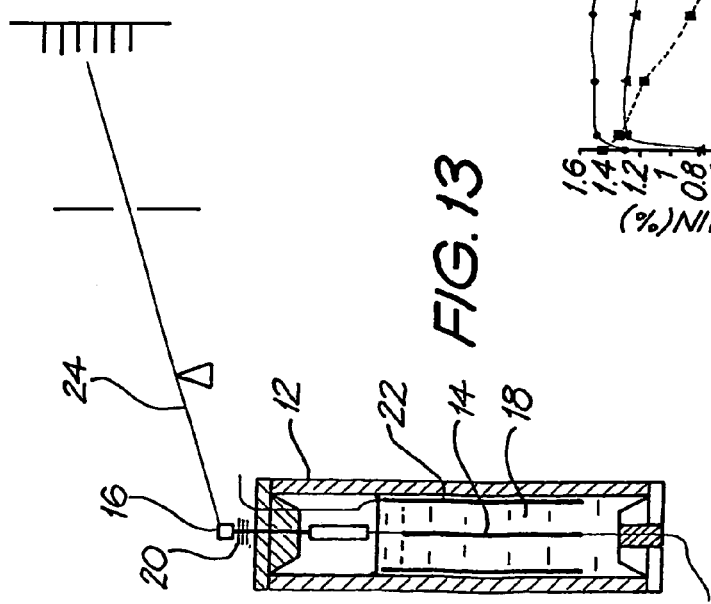

ELECTROMECHANICAL ACTUATOR AND METHODS OF PROVIDING SAME

FIELD OF THE INVENTION

The present invention relates to an electromechanical actuator of the type utilizing a conducting polymer for effecting a desired action with change(s) in the volume of the polymer in response to an applied potential. The electromechanical actuator finds application in numerous fields of technology. There is also provided a method of providing the electromechanical actuator.

BACKGROUND OF THE INVENTION

Electromechanical actuators based on conducting polymers are known in the art and find use as artificial muscles as well as in a myriad of other applications. Operation of such actuators is achieved by redox processes. The actuators may be arranged for providing a bending motion or a uniaxial force.

The bending or axial force is achieved as a result of volume changes in the conducting polymer upon application of a potential to the polymer. More particularly, the volume changes occur as a result of the injection or expulsion of counter ions into or from the polymer during these processes. For instance, upon electrochemically oxidizing a neutral conducting polymer film by the application of an anodic potential to the polymer in an electrolyte, positive charges are generated along the polymer resulting in counter ions being forced to enter the polymer from the electrolyte. As a result, there may be a significant increase in the volume of the conducting polymer. During reduction with a change in the potential, electrons are injected into the solid eliminating the positive charges and forcing the counter ions and solvated molecules to be expelled into the electrolyte. The result of this is that the volume of the conducting polymer decreases and the polymer returns to its neutral state. By harnessing the changes in volume, the electromechanical actuator can be utilized to achieve the desired action such as in the case of an artificial muscle. The expansion and contraction movement of the conducting polymer may also be utilized such as for example, for operating a piston in a miniature pump and other mechanical type applications.

However, attempts to improve the efficiency of performance of electromechanical actuators can impact on the mechanical and/or electromechanical properties of the actuator. It is, therefore, desirable to enhance efficiency of performance while minimizing any impact on the mechanical and/or electromechanical properties of such actuators.

SUMMARY OF THE INVENTION

It is an aim of the present invention to ameliorate one or more of the problems of the prior art or to at least provide a useful alternative.

In a first aspect of the present invention there is provided an electromechanical actuator for effecting a desired action, comprising:

a conducting polymer and a conductor for conducting voltage along the polymer from one end region of the polymer to an opposite end region of the polymer, wherein the conductor is adapted for axially extending and retracting with axial expansion and contraction of the polymer, and extends along the polymer from the first end region to the opposite end region.

Typically, the conductor will be arranged for extending and retracting with axial expansion and contraction of the polymer. Hence in another aspect of the present invention there is provided an electromechanical actuator for effecting a desired action, comprising:

a conducting polymer and a conductor for conducting voltage along the polymer from one end region of the polymer to an opposite end region of the polymer;

wherein the conductor is arranged for axially extending and retracting with expansion and contraction of the polymer, and extends along the polymer from the first end region to the opposite end region.

Preferably, the conductor will be wound in a helix along the polymer. However, it will be understood that the conductor may be arranged in other configurations that allow the conductor to axially extend and contract in concert with the polymer. For example, the conductor may be arranged in a concertina pattern along the polymer.

Accordingly, in another aspect of the present invention there is provided an electromechanical actuator for effecting a desired action, comprising:

a conducting polymer and a conductor wound in a helix along the polymer for conducting voltage from one end region of the polymer to an opposite end region of the polymer.

Typically, the conductor of an actuator of the present invention will extend along a majority of the length of the conducting polymer and most preferably, along substantially the entire length of the conducting polymer.

Typically, the conductor will be in intimate contact with the conducting polymer along substantially the entire length of the polymer. Preferably, the conductor will be embedded in the polymer.

Preferably, the conducting polymer will be in the form of a tube. The tube may have a cross-section lying in a plane extending substantially perpendicularly to a longitudinal axis of the tube of any desired shape. Generally, the shape of the cross-section of the tube will be substantially circular.

Hence, in another aspect of the present invention there is provided an electromechanical actuator for effecting a desired action, comprising a tube of conducting polymer having an internal passageway for receiving an electrolyte.

Preferably, the electromechanical actuator will further comprise an electrical connector for facilitating electrical connection to the conductor. Typically, the connector will also be in direct electrical contact with the polymer. Most preferably, an electrical connector will be connected to each end region of the conductor, respectively.

If desired, the further electrical connector may also be in direct electrical contact with the polymer at a spaced distance from the first mentioned electrical connector.

An actuator as described above may be arranged within an outer actuator comprising a tubular conducting layer allowing bundling of the actuators together.

Accordingly, in another aspect of the present invention there is provided an electrochemical actuator for effecting a desired action, comprising:

an outer actuator comprising a tubular conducting polymer having a hollow interior;

an inner actuator comprising a further conducting polymer; and an electrolyte in a space defined between the inner actuator and the outer actuator;

wherein the actuator is arranged within the outer actuator and lies along the hollow interior of the outer actuator for axial extension or retraction within the outer actuator.

In yet another aspect of the present invention there is provided an electromechanical actuator for effecting a desired action, comprising;

an outer actuator comprising a tubular conducting polymer having a hollow interior;

an inner actuator comprising a further conducting polymer and a conductor for conducting voltage along the further polymer from one end region of the further polymer to an opposite end region of the further polymer; and an electrolyte in a space defined between the inner actuator and the outer actuator;

wherein the conductor is adapted for axial extension or retraction with expansion or contraction of the further polymer and the inner actuator is arranged within the outer actuator and lies along the hollow interior of the outer actuator for axial extension or retraction within the outer actuator.

Preferably, the inner actuator will be arranged within the outer actuator for extension or retraction of the further conducting polymer in opposition to axial expansion or contraction of the tubular conducting polymer.

In another aspect of the present invention there is a method of providing an electromechanical actuator for effecting a desired action, comprising:

arranging a conductor for conducting voltage along a conducting polymer from one end region of the polymer to an opposite end region of the polymer and so that the conductor extends along the polymer from the one end region to the opposite end region for axially extending and contracting with expansion and contraction of the polymer.

Typically the method will further comprise embedding the conductor in the polymer. This may be achieved by coating the conductor with polymer using any suitable method known in the art.

An electrochemical actuator of the invention may for instance be manufactured by winding the conductor around a temple to form a helix along the template and subsequently coating the template and/or the helix with polymer. Preferably, the polymer will be coated on the conductor by electrodeposition.

Most preferably, the conducting polymer will be electrodeposited onto the template and the conductor.

Hence, in another aspect the present invention extends to a method of providing an electromechanical actuator for effecting a desired action, comprising:

electrodepositing a conducting polymer onto a conductor wound in a helix to form a tube of the polymer in which the helix is embedded.

In yet another aspect of the present invention there is provided a method of providing an electromechanical actuator for effecting a desired action, comprising:

(a) winding a conductor around a template to form a helix along the template; and (b) electrodepositing a conducting polymer onto the helix to form a tube of the polymer in which the helix is embedded;

wherein the helix is in electrical contact with the tube of polymer for conducting a voltage along the tube from one end region of the tube to an opposite end region of the tube.

Typically, the conducting polymer will be electrodeposited onto the helix while the helix is wound around the template. Preferably, the method will further comprise the steps of:

(c) removing the template from the helix;

(d) connecting an electrical connector to one or each end region of the conductor respectively, for facilitating electrical connection with the conductor; and (e) securing the conductor to the or each electrical connector.

Preferably, an electrical connector will be inserted into the one end region of the polymer and another said electrical connector into the opposite end region of the polymer.

In yet another aspect there is provided a method of providing an electromechanical actuator for effecting a desired action, comprising:

forming a polymer body on a conductor for conducting voltage along the polymer body from one end region of the polymer body to an opposite end region of the polymer body and axially extending and retracting wit expansion and contraction of the polymer body.

In another aspect of the present invention there is provided an electrochemical actuator for effecting a desired action, comprising;

a tube of conducting polymer having a longitudinal passageway for receiving an electrolyte.

In still another aspect of the present invention there is a method for providing an electrochemical actuator for effecting a desired action, comprising:

coating a template with a conducting polymer; and removing the template to provide a tube of the polymer having a longitudinal passageway for receiving an electrolyte.

Generally, one end of the electromechanical actuator of the invention will be adapted for being secured to a support and an opposite end for being secured to a load in order to effect the desired action. The support and/or the load may be movable by the actuator relative to a fixed reference point upon actuation of the electromechanical actuator in use.

The conducting polymer may be any polymer capable of undergoing a volume change and/or change in one or more mechanical properties (eg. stiffness) in response to redox processes and which is deemed suitable for use in the provision of an electromechanical actuator of the type to which the present invention relates. The polymer may comprise a polymeric material consisting of a single polymer or a mixture of a number of different polymers. Accordingly, the term "conducting polymer" is to be taken to include within its scope a mixture of polymers one or more of which are capable of undergoing redox processes.

The conductor used for conducting voltage along the polymer will typically have greater conductivity ($\kappa$) compared to the conducting polymer utilized. The conductor may be formed from any material deemed suitable. For example, the conductor may be another conducting polymer such as a polyaniline fiber or thread. Preferably, however, the conductor will be a metal such as platinum, gold, silver or other metal with sufficient flexibility to extend and contract in concert with expansion and contraction of the conducting polymer. Most preferably, the conductor will be a wire.

Preferably, the template will also be conductive and most preferably, will be a length of metal such as a metal strip, wire or the like. Generally, the template will consist of the same material as used for the conductor.

The electrical connector(s) may be any short length of conducting metal. Preferably, the or each electrical connector will consist of the same material as used for the conductor.

The conductor will generally be secured to the or each electrical connector by wrapping the connector tightly around the connector(s) or by gluing, heat welding or other suitable means. Preferably, the conductor will be glued to the connector(s) by a suitable epoxy resin.

By forming the conducting polymer in the shape of a tube, it has been found that improved characteristics of the actuator may be obtained compared to the conducting polymer when provided in strip form. In particular, one or more of the electronic, mechanical and/or electrochemical properties of the actuator may be enhanced. While not being bound by theory, it is believed that a tube configuration has enhanced electrolytic efficiency compared to an actuator in the form of a strip as more of the conducting polymer comprising the tube is electrochemically accessible than a corresponding strip of the polymer.

It is further believed the provision of the conductor further enhances electrolytic efficiency by reducing voltage (iR) drops along the conducting polymer, enabling longer fibers to be used while retaining efficient activation capability.

Electromechanical actuators of the present invention find use in a broad range of applications. For example, an electromechanical actuator may be utilized as an artificial muscle in prosthetic or robotic applications, as an actuator in pumps for microfluidic applications, as an actuator in anti-vibration systems, as an actuator for electronic Braille screens, as an actuator in medical devices such as steerable catheters, and fibers in wearable prosthetics such as gloves that assist in gripping. Accordingly, an electromechanical actuator may be woven into a fiber or mesh, or otherwise lie along and be secured to fabric or mesh for causing movement of same upon actuation of the actuator.

Accordingly, in another aspect, there is provided apparatus incorporating an electromechanical actuator of the present invention. The electromechanical actuator will typically be provided in a suitable electrolyte. The electrolyte may be a liquid or solid electrolyte, and the actuator may be immersed in the electrolyte or otherwise coated with the electrolyte.

In yet another aspect of the present invention there is provided a device incorporating an electromechanical actuator for effecting a desired action together with an electrolyte, wherein the electromechanical actuator comprises:

A conducting polymer and a conductor for conducting voltage along the polymer from one end region of the polymer to an opposite end region of the polymer, wherein the conductor is adapted for axially extending and retracting with expansion and contraction of the polymer, and extends along the polymer from the one end region to the opposite end region.

Preferably, the electrolyte will be an ionic liquid electrolyte. Most preferably, the ionic liquid electrolyte will comprise an ionic liquid selected from the group consisting of 1-ethyl-3-methyl imidazolium bis(trifluoromethanesulfonyl) amide (EMI.TFSA) and 1-butyl-3-methylimidazolium hexafluorophosphate ($MBI.PF_6$).

Hence, in still another aspect of the present invention there is provided a device incorporating an electromechanical actuator for effecting a desired action together with an ionic liquid electrolyte, wherein the electromechanical actuator comprises:

a conducting polymer and a conductor for conducting voltage along the polymer from one end region of the polymer to an opposite end region of the polymer;

wherein the conductor is adapted for axially extending and retracting with expansion and contraction of the polymer, and extends along the polymer from the one end region to the opposite end region.

Unless the context clearly requires otherwise, throughout the description and the claims, the words 'comprise') 'comprising', and the like are to be construed in an inclusive sense as opposed to an exclusive or exhaustive sense; that is to say, in the sense of "including, but not limited to".

The features and advantages of the present invention will become further apparent from the following description of preferred embodiments of the invention.

BRIEF DESCRIPTION OF THE ACCOMPANYING DRAWINGS

FIG. 13 illustrates a two electrode cantilever test system for measuring electromechanical actuator displacement;

FIG. 14 is a graph showing strain versus cycle number observed for a polymer actuator in propylene carbonate (0.25 M $TBA.PF_6$) and two separate ionic liquids.

Figure 15:
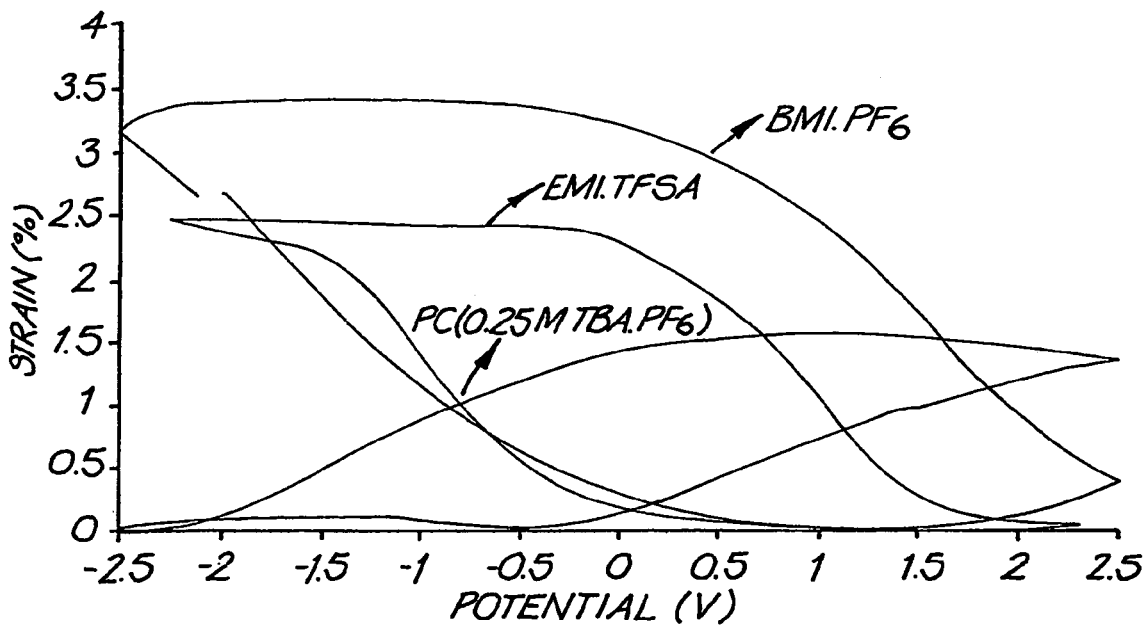
Figure 16:
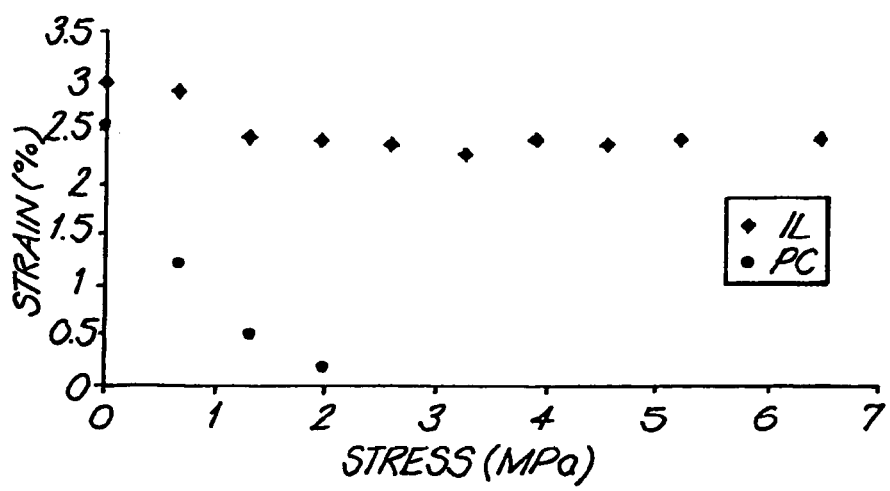

FIG. 15 is a graph showing strain potential curves for an electromechanical actuator of the present invention following application of a +2.5V cyclic wave form with a scan rate of 50 mV/s; and FIG. 16 is a graph showing strain observed under load for $PPy.PF_6$ in EMI.TFSA (IL2) compared to propylene carbonate electrolyte (containing 0.25 M $TBA.PF_6$) using a triangular waveform (+2.5V) applied at a scan rate of 50 mV/s.

DETAILED DESCRIPTION OF PREFERRED EMBODIMENTS OF THE INVENTION

Inherently conducting polymers (ICPs) such as polypyrroles, polythiophenes and polyanilines (I-III shown below) have attracted considerable attention over the past two decades.

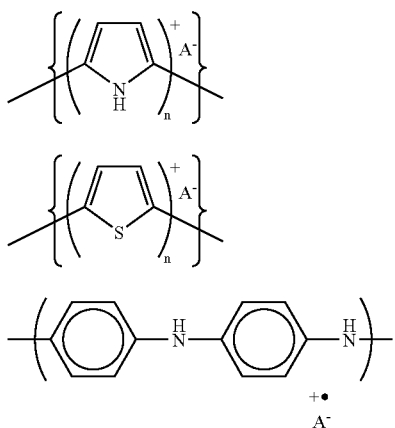

(I)

(II)

(III)

The electronic and ion exchange redox properties of these materials has led to their use in application areas as diverse as chemical sensors, polymer batteries, polymer containing supercapacitors, membrane separations and artificial muscles. All of these applications utilise the chemical or physical changes that accompany the facile redox processes occurring at these polymers.

Electromechanical actuators based on inherently conducting polymers can be viewed as simple electrochemical cells in which the application of a potential creates dimensional changes in one or more of the electrode materials. The ability to efficiently inject or extract charge from the polymer(s) utilised without mechanical degradation of the system determines the overall actuator performance possible. Hence, the electrochemical properties of polymer(s) utilised dictate the level of performance obtainable.

Conducting polymers are oxidised/reduced according to Equations (1) and (2) set out below using polypyrrole as an example:

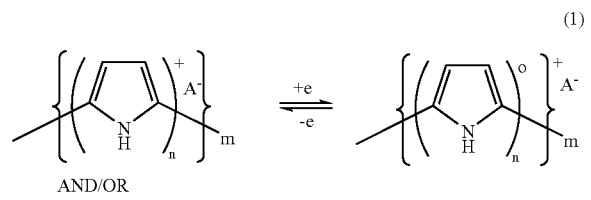

(1)

AND/OR

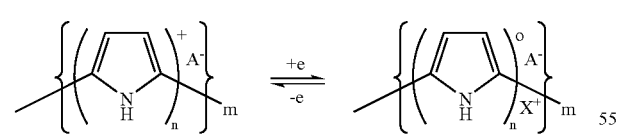

(2)

$A^-$ is a dopant anion, $X^+$ is a cation from the supporting electrolyte, n is an integer of from 1 to X and is most usually 3 or 4. The symbol m represents the number of repeat units of the polymer thereby determining the molecular weight of the polymer.

Figure 1:
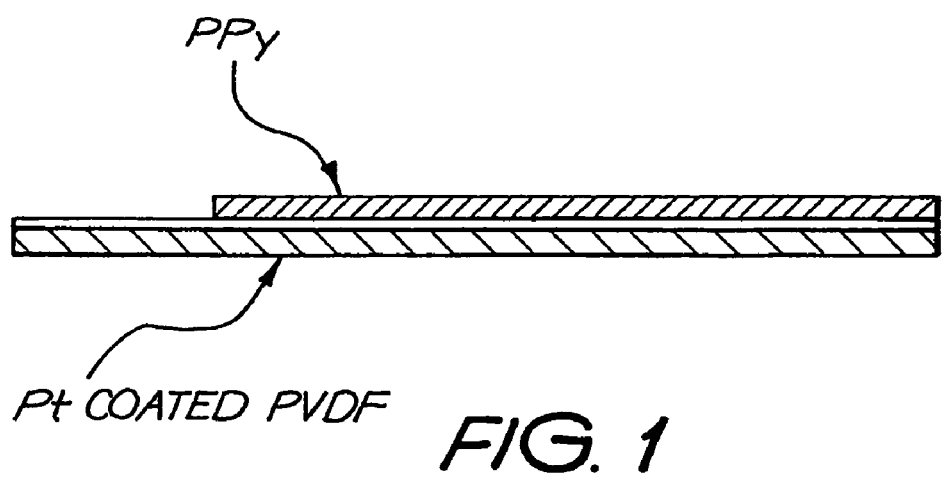
FIG. 1 is a schematic representation of a electromechanical actuator in the form a bimorph comprising a laminate structure formed by electrochemically polymerising polypyrrole (PPy) onto a platinum coated PVDF membrane.
Figure 2:
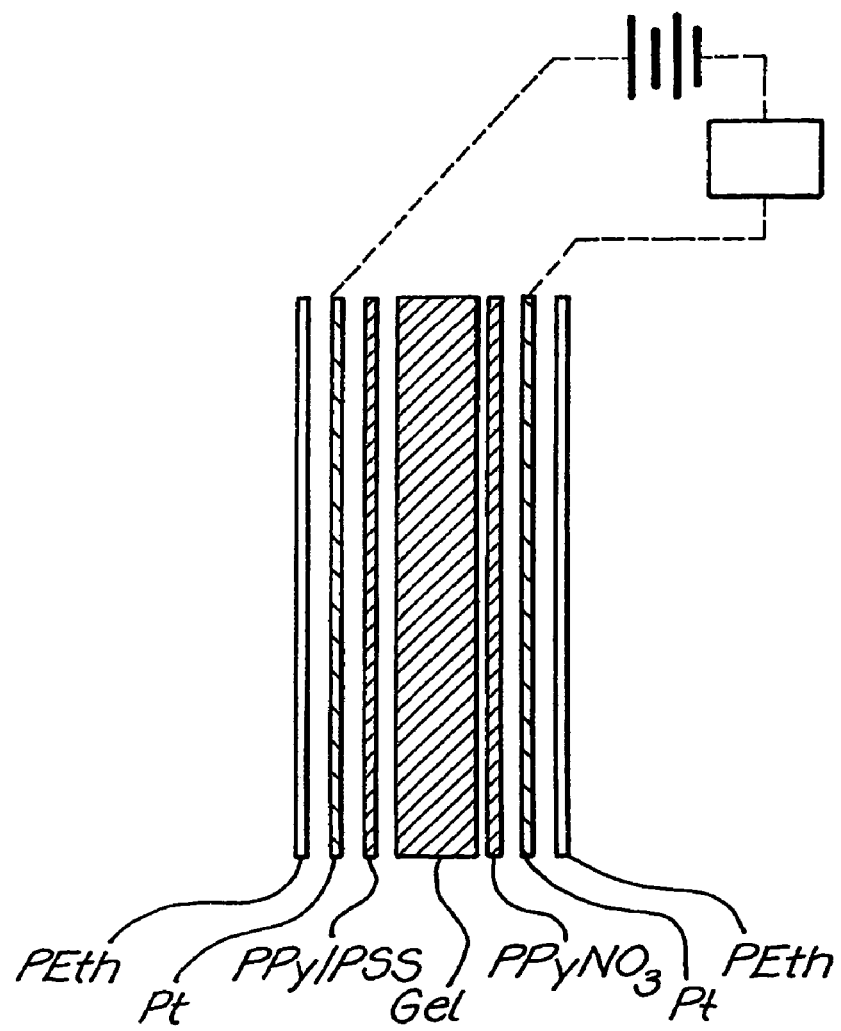
FIG. 2 is a schematic representation of an axial force electromechanical actuator.

For small mobile anions ($A^-$) the process described by Eq. 1 predominates whereas for larger immobile anions (such as polyelectrolytes), processes described by Eq. 2 will predominate. In practice, for most anions, a mixture of both processes occurs. Accompanying anion expulsion (Eq. 1) is a decrease in volume of the conducting polymer. Alternatively, if cations are incorporated into the polymer (Eq. 2) during the redox reaction, the volume of the polymer increases[1]. These dimensional changes may be translated into a bending motion using a bimorph[2] as illustrated in FIG. 1, or a uniaxial force[3] using an appropriate configuration as for example illustrated in FIG. 2.

To maximise energy efficiency, the conducting polymer should be oxidised/reduced at minimal potentials and the process not be limited by kinetic effects. However, with all conducting polymers the latter is an inherent limitation since movement of ions through the electrolyte and polymer is diffusion controlled.

Transitions induced by polymer oxidation/reduction may have an effect on the ability of a polymer to actuate[4]. For instance, a polymer becomes more resistive (that is, resistance R increases) with electrochemical reduction making subsequent reduction or oxidation more difficult since:

$$E = Eapp - iR \quad (3)$$

where E is the potential at the polymer, Eapp is the potential applied by an external power source and i is the current. Change in the electronic properties of the polymer makes efficient charge injection throughout the polymer, especially to the reduced state, desirable.

Chemical properties of a polymer can also change dramatically with properties such as hydrophobicity being dependent on the oxidation state[4]. This, in turn, influences which electrochemical mechanism (Eq. 1 or 2) predominates. For example, if hydrophobicity of a polymer dramatically increases upon reduction it is easier to extract anions from the polymer than inject highly hydrated cations into the polymer.

In addition, mechanical properties of a polymer can be greatly influenced by lie potential applied[5] and hence, the redox state of the polymer. In this regard, a polymer can become significantly more ductile in the reduced state, and such changes in mechanical properties may well influence the efficiency of an electromechanical actuator.

The above illustrates that actuator performance and efficiency are dependent on the ability to inject or extract charge from the polymer with low energy consumption. The ease of charge injection/extraction is reflected in a parameter denoted as electrolytic efficiency (EE). The electrolytic efficiency is a measure of the ability to access all the available electrochemical sites of a polymer that can contribute to actuation. Specifically, the electrolytic efficiency of a system can be defined as:

$$EE_{ox} = \frac{\text{Charge passed during oxidation}}{\text{Charge for complete oxidation}^{(a)}} \times 100$$

$$EE_{red} = \frac{\text{Charge passed during reduction}}{\text{Charge for complete reduction}^{(a)}} \times 100$$

(a) Estimated from charge consumed during growth and assuming n=3 in Eqs. (1) and (2).

Figure 3:
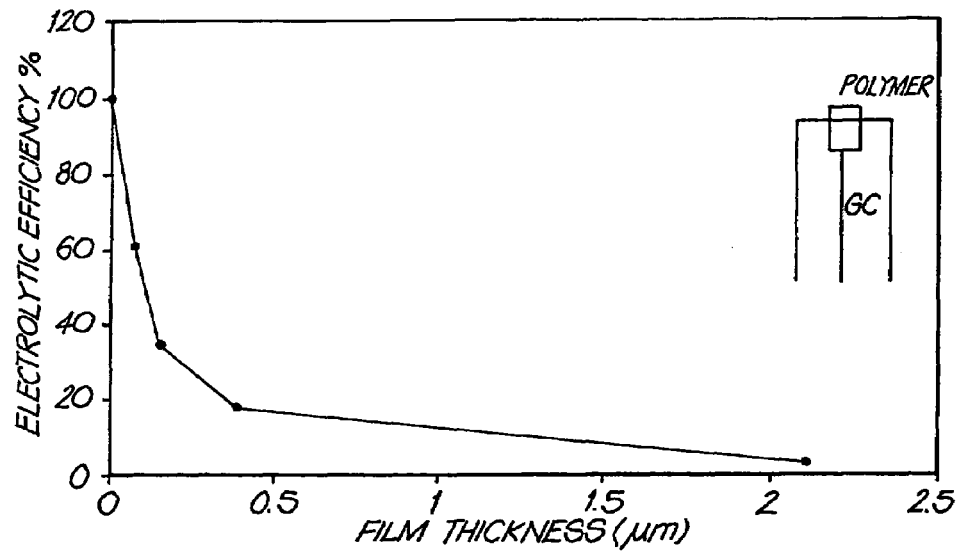
FIG. 3 is a graph of electrolytic efficiency against polymer thickness of a film of polypyrrole on a glassy carbon disc electrode obtained using an applied voltage of −1.0 V~+0.50 V with a pulse width of 250 msec.

The effect of polymer thickness on electrolytic efficiency of a polymer film deposited on a glassy carbon disc electrode (ie. with substantially ideal electrical connection) is shown as a function of polymer thickness in FIG. 3. The polymer used in this study was polypyrrole. From the graph, it is clear that only a very thin film (<0.27 μm) gave high electrolytic efficiency. This corresponds to an electrode contact surface area to polymer volume ratio of $3.7 \times 10^4$ $cm^2/cm^3$. Generally, however, only free-standing films of a thickness greater than about 4 µm have adequate mechanical properties for actuation.

While the polymer(s) and electrolyte used determine the maximum performance of an electromechanical actuator that can be expected, practical issues such as the efficiency of the electrical connection to the actuator may also be a limiting factor.

Figure 4A:
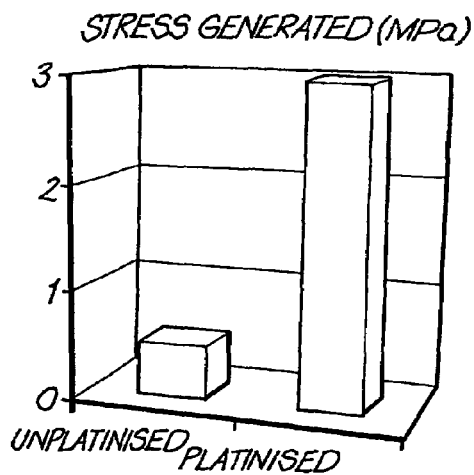
FIG. 4a is a graph comparing stress generated by unplatinised and platinised polypyrrole films.
Figure 4B:
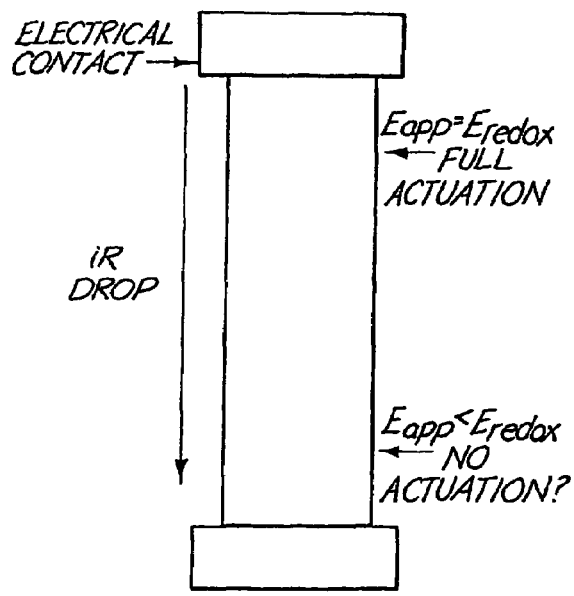
FIG. 4b is a schematic diagram illustrating the effect of iR (voltage) drop on the actuation of polypyrrole film.

Improvement in actuation performance may be obtained by platinizing a conducting polymer film in order to minimize iR (ie voltage) drop effects along the length of the actuator as indicated in FIG. 4(a) and 4(b). In particular, an unplatinized polymer film was found to produce approximately 0.5 MPa stress during isometric testing. In contrast, when contraction was induced by electromechanical stimulation, an identical platinized film generated 3 MPa stress.

For most efficient performance an actuator should not only allow efficient injection and extraction of charge, but should also desirably enhance or at least not interfere with the mechanical and electromechanical properties of the device. In the example illustrated in FIG. 4, although enhanced electrical connection to the polymer was obtained, the coating of the polymer with platinum (sputter coating) markedly decreased the strength of the polymer film.

The electrolyte used to facilitate the redox processes plays an important role. If the original dopant anion (A$^-$) shown in the above examples is released during the reduction process, subsequent ICP oxidation will involve uptake of electrolyte anions. If on the other hand the reduction process leads to cation (X$^+$) incorporation that is, the anion is not expelled during reduction, then X$^+$ will be taken up from the electrolyte source.

The electrolyte also plays an important role in determining the performance of ICPs at extreme potentials. In particular, at extreme anodic potentials polypyrroles undergo irreversible degradation which is attributed to nucleophilic attack on the polymer from solvent or electrolyte ions. Breakdown of the solvent or electrolyte can also prevent some of the electronic properties of ICPs from being accessed. For example, at extreme negative potentials some polythiophenes can be n-doped[18-20] provided the solvent or electrolyte does not break down before this occur.

Interestingly, the electrolyte can also have a direct impact on the mechanical properties of ICPs even after simple immersion before any electrical stimuli are applied. Variation in mechanical properties as the oxidation state of the polymer is changed has also been found to be electrolyte dependent.

In some electrochemical systems containing ICPs the use of conventional liquid electrolytes is not practical, with leakage or loss due to evaporation resulting in limited working life. Thus, there is a need for alternative systems. For example, both polyvinylalcohol (containing $H_3PO_4$) and polyethylene oxide (containing $LiCF_3SO_3$) platicised with poly(ethylene) glycol have been evaluated for use in polypyrrole based redox supercapacitors with specific capacitances in the range 40-84 $Fg^{-1}$ being obtained. These electrolytes have ionic conductivities in the range $10^{-4}$-$10^{-3}$ $Scm^{-1}$. Alternatively, polyethylene oxide-based solid polymer electrolytes have been used in polypyrrole based batteries[7].

Figure 5:
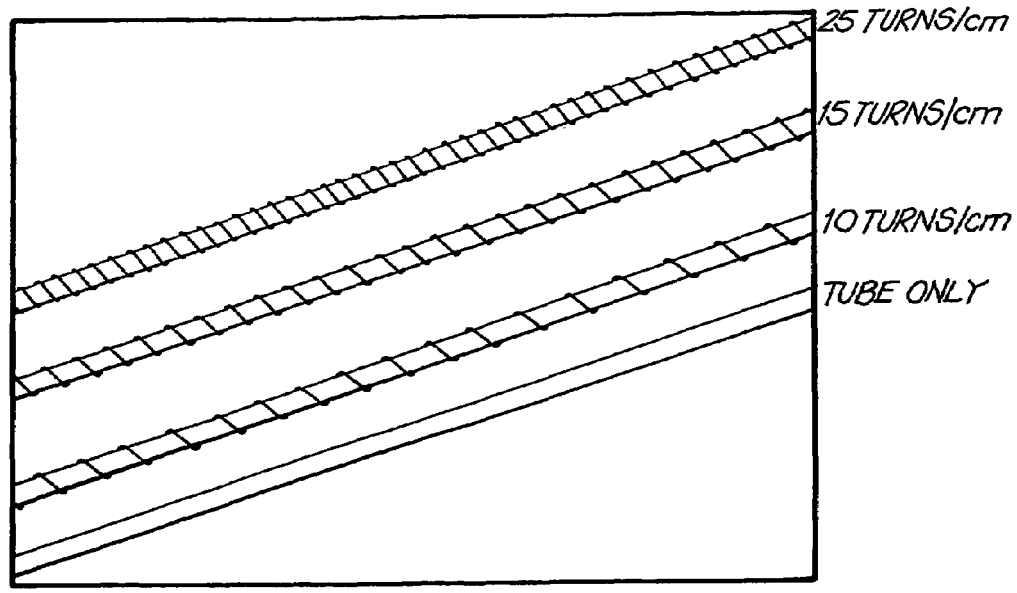
FIG. 5 is a partial side view of electromechanical actuators embodied by the present invention.

Actuators of the present invention are illustrated in FIG. 5. In particular, the embodiment illustrated by A comprises a tube of polypyrrole (PPy) alone. The filer actuators indicated by B, C and D comprise a tube of the polymer incorporating a longitudinally extending helix formed by a conductor comprising platinum wire. While platinum is used in the present example, the wire may be made from other suitable metals. Indeed, the wire may be formed from conducting materials other than metal. In the actuators shown, the pitch of the helical wire for embodiment B is 10 turns cm$^{-1}$, while the pitch for embodiments C and D is 15 turns cm$^{-1}$ and 25 turns cm$^{-1}$, respectively.

The manufacture the actuator will now be described with reference to FIG. 6. Briefly, a conductor comprising a 25 µm platinum wire 2 is wrapped around a straight 125 µm platinum wire template to form a helix therealong. The conductor and template wires are then placed in a polymer electrolyte solution and electroplated for 24 hours at –28° C. to form a tube of polymer around the template wire 4 and conductor wire 2 as indicated in step (C), prior to removing the formed polymer tube from the electrolyte solution as indicated in step (D). The template wire 4 is then slid from the polymer tube 6 prior to electrical connectors in the form of short inserts 8 and 10 of 125 µm platinum wire being inserted into each end 12 and 14 of the polymer tube as indicated in steps (E) and (F). Each end of the connector wire 4 is then wrapped tightly around the corresponding short wire insert 8 or 10, and fixedly glued in position thereon by an epoxy resin as indicated in step (G).

If desired, the template wire 4 may be left in position within the longitudinally extending interior passageway of the polymer tube rather than removing it as indicated above.

Figure 7:
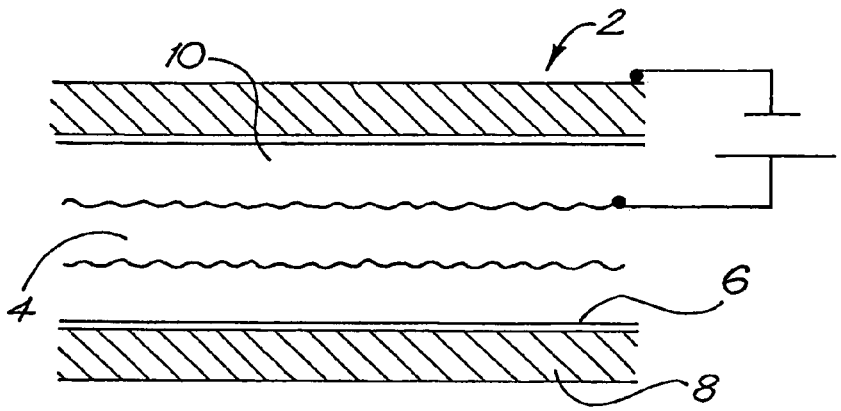
FIG. 7 is a schematic diagram illustrating a device incorporating an electromechanical actuator of the present invention.

A further embodiment of an electromechanical actuator of the present invention is illustrated in FIG. 7. This device comprises an outer actuator 2 which receives an inner actuator 4. The device therefore has a tube in tube configuration. The outer actuator comprises a hollow permeable membrane fiber 6 composed of polypropylene or other suitable material. The outer actuator is formed by first metalizing the permeable membrane fiber utilizing a suitable metal such as platinum. This may be achieved by sputter coating the selected metal onto the fiber using conventional sputter coating techniques. A layer of conducting polymer 8 (eg polypyrrole) is then electrodeposited on to the metal coating. However, it will be understood that the coating of the polymer may be achieved by other methods. For instance, the metalized fiber could be dipped into a suitable molten conducting polymer. The inner actuator 4 comprises a tubular actuator of the type shown in FIG. 5 incorporating a helical wire conductor embedded in the wall of the actuator. The space 10 between the inner actuator 2 and the outer actuator 4 is filled with an ionic liquid electrolyte.

In use, the device is connected to a power supply such that the inner actuator functions as the cathode and the outer actuator the anode. Accordingly, when a voltage is applied, the inner actuator 4 axially expands and the outer actuator axially retracts. The inner and outer actuators therefore move axially in opposition to one another. The arrangement provides enhanced efficiency as the same electrolyte is used for obtaining axial movement of both actuators. The conducting polymers of the inner and outer actuators may be the same or different.

Figure 6:
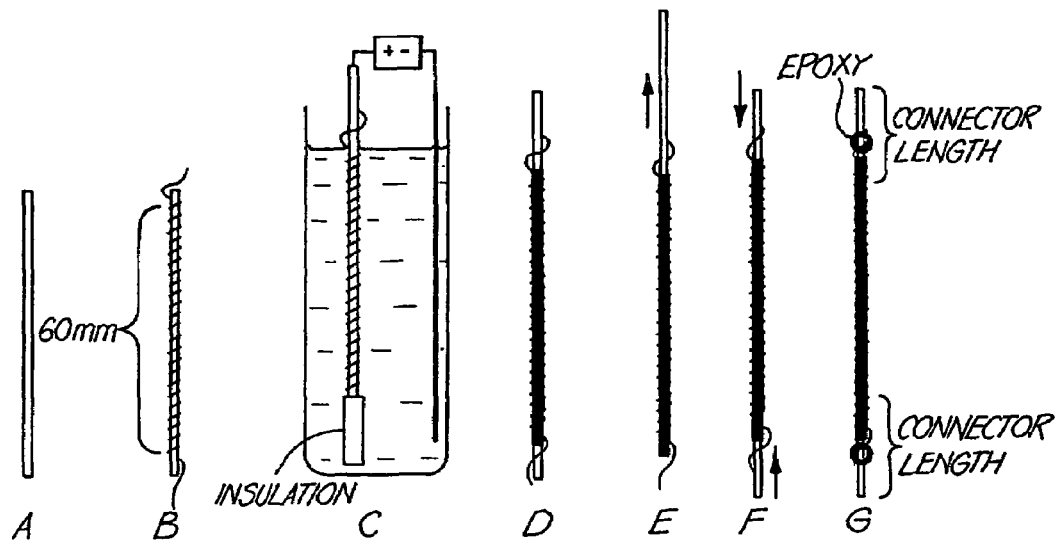
FIG. 6 is a schematic representation illustrating the manufacture of an electromechanical actuator of the present invention.

As will be appreciated, rather than an outer actuator as illustrated in FIG. 7, an outer actuator with a helical wire conductor extending along its length of the type shown in FIG. 6 may be used. That is, one or both of the inner and outer actuators may incorporate a helical conductor, respectively. It will also be understood that reversing the direction of actuation of the inner and outer actuators may be achieved by reversing the polarity of the applied potential. Alternatively, the outer actuator may incorporate a helical conductor and no the inner actuator.

Suitable polymers that may be used in an actuator of the present invention include, but are not limited to polyaniline, polypyrrole and polythiophene, derivatives thereof, and mixtures of the foregoing.

Suitable derivatives include alkyl, alkoxy, amine and alcohol derivatives of polyaniline, polypyrrole, polythiophene. Such derivatives are well known in the art. Examples include poly(3-alkylthiophene)s, poly(3-alkylpyrrole)s, poly(methoxyaniline)s and poly(alkylaniline)s. Specific polymers that may find use in electromechanical actuators of the present invention include poly(3,4-ethylenedioxypyrrole), poly(3-heptoxythiophene), poly(3-dodecylthiophene), poly(2,5-dimethoxyaniline), poly(2,2-bithiophene) and poly(3,4-ethylenedioxythiophene) Of particular interest are inherently conducting polymers containing redox groups such as ferrocene that introduce additional charge (and thereby expansion) capacity such as for example poly[(3-ferrocenylpropyl) pyrrole]. Copolymers containing any of the monomers identified above are may also find application in an electromechanical actuator of the present invention.

In addition, blends of polymer systems may also be utilized. Blends of polymers may be obtained by mixing inherently conducting polymers with polyvinyl alcohol, polymethacrylate, poly(butylacrylate-vinyl acetate), polyurethane or polyester. Such blends may be used to improve the mechanical properties of the overall material and provide more processing options. Inherently conducting polymers containing selected additive components such as metallic fibers, particles or carbon nanotubules to improve strength and/or conductivity may also be utilized.

A range of dopants ($A^-$) may also be incorporated into the conducting polymers such dopants are well known in the art. Of particular interest are those dopants that increase mechanical strength of the polymer such as sulphated poly ($\beta$-hydroxy ether) when used in polythiophenes and dopants incorporating redox groups such as poly(1-vinyl ferrocene-2-sulfonate) which may improve performance of the actuator.

While the conducting polymer may be electrodeposited onto the conductor of an actuator of the invention, the coating of the polymer may be achieved by any other suitable method. For instance, as indicated above, the conductor may be coated with the polymer by dipping the conductor into molten polymer. Alternatively, soluble polymers may be cast around the conductor and polymers that melt may be extruded around the template and conductor.

Desired characteristics of an electrolyte for use in electromechanical actuators include adequate conductivity, mechanical properties, adhesion during flexing and mechanical/electrical stability, easily processible and that the electrolyte be able to function in air. An electrolyte may for instance be contained in a porous membrane or a gel such as a polyacrylamide gel. Suitable electrolyte systems are also conventionally known in the art and any appropriate electrolyte may be utilized. For example, polyethylene glycol containing $LiClO_4$ has been used in the past as a solid polymer electrolyte for polypyrrole based microactuators[8]. The use of polyacrylonitrile or Kynar based non-aqueous electrolytes and water based polyacrylamide hydrogel ion source/sinks containing various perchlorate salts have also been investigated for their applicability in polypyrrole based actuators[9]. Those studies indicated that the optimum electrolyte for use with polypyrrole based actuators was a polyacrylonitrile plasticized with propylene carbonate and ethylene carbonate containing 1.0 M $NaClO_4$.

Further examples of electrolytes that may be used include simple salt electrolytes such as sodium chloride solutions and salt containing buffers. The salt concentration is typically in a range of from 0.1 to 1.0 M. Buffers that may be utilised include 0.1 to 1.0 M phosphate and acetate buffers.

Organic electrolytes such as acetonitrile or polypropylene carbonate containing salts such as tetraethyl ammonium hexafluorophosphate in a concentration typically in a range of from 0.1 to 0.25 M may also be used.

The pH of an electrolyte will depend on the inherently conducting polymer used. For polypyrrole and derivatives of this polymer, the pH will typically be in a range of from pH 2 to 7.

Preferred electrolytes also include ionic liquids (organic salts that are molten at or about room temperature) and particularly ionic liquids containing polymers. Ionic liquids function well as electrolytes in electrochemical actuator systems and have excellent environmental and electrochemical stability. Indeed, it has been shown that dramatically improved electromechanical efficiency and lifetime can be achieved when ionic liquids are used as the electrolyte in artificial muscle systems based on ICPs and that electrochromic windows based on ICPs using ionic liquids as electrolyte can be cycled in excess of 1,000,000 times[10]. Examples of ionic liquid electrolytes include 1-butyl-3-methyl imidazolium hexafluorophosphate ($BMI.PF_6$) and 1-ethyl-3-methyl imadazolium bis(trifluoromethanesulfonyl)amide (EMI.TFSA) and combinations of the cations and anions indicated in Scheme 1.

Scheme 1:
Examples of Ionic Liquid Components (I)

$[NR_xH_{4-x}]^+$
Alkylammonium cation (II)

$[PR_xH_{4-x}]^+$
Alkylphosphonium cation (III)

N,N'-dialkylimadazolium cation (IV)

N-alkylpyridinium cation (V)

Pyrrolidinium cation (VI)

$PF_6^-$ (VII)

$BF_4^-$ (VIII)

$CF_3SO_3^-$

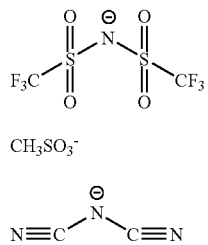

(IX)

(X)

CH$_3$SO$_3^-$ (XI)

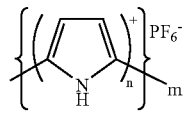

The invention will now be further described with reference to a number of examples.

EXAMPLE 1

For the purpose of demonstrating characteristics of electromechanical actuators of the invention, a number of actuators were prepared and tested using polypyrrole polymer with hexaflourophosphate (PF$_6^-$) as a dopant as indicated below.

wherein n=2-4, and m=the number of repeat units of the polymer.

Specifically, the actuators were prepared:

(a) as a strip by electrodeposition onto a platinum (Pt) plate from a solution containing 0.06 M pyrrole and 0.05 M PPy/PF$_6$ in propylene carbonate at a current density of 0.15 mA/cm$^2$;

(b) as a tube but with no helical wire conductor 2 using the method described above the reference to FIG. 6 and the solution and electrochemical conditions as for the preparation of the strip actuator in (a) above;

(c) as a tube with a helical wire conductor 2 using the method described above with reference to the FIG. 6 and using the solution and electrochemical conditions as for the preparation of the strip actuator as in (a) above.

The tube configuration results in improved electronic, mechanical and electrochemical properties as summarised below in Table 1. Mean values are shown.

TABLE 1

Characteristics of tube actuator compared to flat film actuator

|  | Tube (no helix) (PPy/PF$_6$) | Flat Film (PPy/PF$_6$) |
| --- | --- | --- |
| Conductivity (Scm$^{-1}$) | 170 | 85 |
| Tensile strength (MPa) | 23 | 6.0 |
| Elongation to break (%) | 17 | 8.0 |
| Electrolytic efficiency (%) | 10 | 5.0 |

The electrochemical efficiency of the tube configuration compared to the flat film indicates that more of the tube is electrochemically accessible than the corresponding strip. However, even with the tube configuration, enhanced electrolytic efficiency and actuation was obtained with just one and then both ends of the tube connected to the short wire inserts 8 and 10 suggesting improved electrical connection with the polymer was obtained utilising the wire inserts as indicated in Table 2.

TABLE 2

Characteristics of tube actuators.

|  | Tube (no helix) One end connected (PPy/PF$_6$) | Tube (no helix) Both ends connected (PPy/PF$_6$) |
| --- | --- | --- |
| Electrolytic efficiency (%) | 3.5 | 5.0 |
| Stroke (strain) (%) | 0.23 | 0.33 |
| Stroke rate (%/sec) | 0.48 | 0.67 |

EXAMPLE 2

A number of tube actuators of the invention incorporating helical conductors were prepared and the performance of three samples is shown in Table 3.

Resistance of the actuators were measured after locating wire inserts 8 and 10 in each end of the polymer tube, respectively.

All the polymer helices were between 45 and 55 mm long.

All polymer helices tested were from the same batch and prepared under a current density of 0.15 mA/cm$^2$ for 24 hours.

A platinum (Pt) wire helix was used with a pitch of 25 turns/cm.

TABLE 3

Comparison of characteristics between the actuators with helical conductor

| Polymer Helix | Resistance (Ω)* | Strain (%) | Strain Rate (%/sec) |
| --- | --- | --- | --- |
| Helix 2 | 4–8 | 0.7 | 1.4 |
| Helix 3 | 4–8 | 0.8 | 1.6 |
| Helix 5 | 4–8 | 0.8 | 1.6 |

In all cases, the inclusion of the helical wire in the actuator resulted in improved electrochemical and actuator performance. By forming the conductor wire 2 into a helix, the wire is able to readily extend and contract in length with expansion and reduction of the volume of the polymer tube.

EXAMPLE 3

Figure 8:
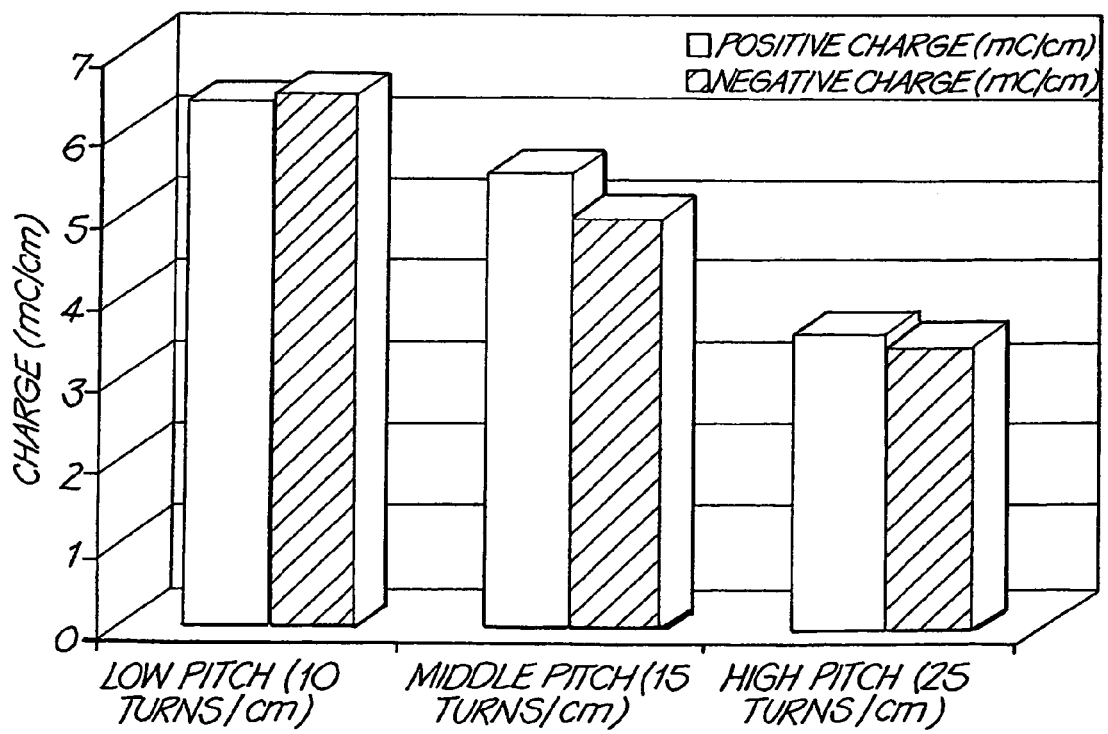
FIG. 8 is a graph showing charges transported by electromechanical actuators of the present invention against pitch of the helix of a conductor of the respective actuators.

The effect of the pitch of the helical wire 2 on actuator performance was investigated. The results set out in Table 4 suggests use of low pitch provides better performance as indicated by the increase in strain obtained. The increase in strain at lower pitch is in agreement with the increase in electrochemical efficiency at lower pitch as indicated in FIG. 8.

TABLE 4

Effects of pitch of helical conductor on strain under different applied frequencies

| | Strain (%) | |
| --- | --- | --- |
| Operating Frequency | Low Pitched (10 turns/cm) | High Pitched (25 turns/cm) |
| 10.0 Hz | 0.10 | 0.1 |
| 5.0 Hz | 0.28 | 0.1 |
| 2.0 Hz | 0.38 | 0.2 |

TABLE 4-continued

Effects of pitch of helical conductor on strain under different applied frequencies
Strain (%)

| Operating Frequency | Low Pitched (10 turns/cm) | High Pitched (25 turns/cm) |
|---|---|---|
| 1.0 Hz | 0.67 | 0.16 |
| 0.5 Hz | 1.0 | 0.1 |

EXAMPLE 4

An actuator was prepared as described in Example 1 and illustrated in FIG. 6. In particular, platinum wire (50 micron) was wound tightly around a 250 micron platinum wire core template. The platinum wire and template were then cleaned with acetone and left to dry in air before use as the working electrode in electropolymerization. Electropolymerization of PPy/PPF6 was performed using an EG & G Princeton Applied Research Model 363 Potentiostat/Galvanostat together with a conventional one compartment electrochemical cell and three electrode system. An Ag/Ag+ reference electrode and platinum mesh auxiliary electrode were used.

All solutions were thoroughly deoxygenated with nitrogen prior to use. A current density of 0.15 mA/cm² was applied. The polymerization solution consisted of propylene carbonate containing 0.06 M pyrrole momomer and 0.05 M tetrabutylammonium hexafluorophosphate (TBA.PF$_6$). 1% (v/v) H$_2$O was added to ensure that the water content was constant. The pyrrole, TBA.PF$_6$ and propylene carbonate were obtained from Sigma Chemical Co. The pyrrole was distilled before use. The cell temperature was controlled at −28° C. The polymerisation process was maintained for 6 hours and a polymer tube formed around the platinum wire template. Following electrodeposition the platinum template was removed. The resulting hollow tube with the helical platinum wire conductor embedded in the inner wall was then washed with propylene carbonate and stored wet.

Electrical connection to the hollow tube was provided using two shorter platinum wires (1-1.5 cm) inserted into each end of the tube and subsequently glued in position with polystyrene hot melt. The electrical contact was checked by measuring the electrical resistance between the two ends. Values of 4 to 8 ohms were typically obtained.

EXAMPLE 5

The use of the ionic liquids BMI.PF$_6$ and EMI.TFSA as electrolytes for the electromechanical actuator prepared in Example 4 was compared with propylene carbonate containing 0.1M tertiary butylammonium hexafluorophosphate (TBA.PF$_6$).

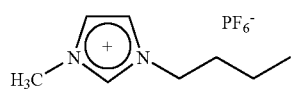

1-butyl-3-methylimidazolium hexaflourophosphate (BMI.PF$_6$) [IL1]

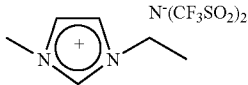

1-Ethyl-3-methyl imidazolium bis(trifluoromethanesulfonyl) amide (EMI.TFSA) [IL2]

Cyclic voltammetry studies were conducted in a three electrode electrochemical cell using a platinum working electrode onto which the PPy/PF6 composite had been deposited. A Ag/Ag$^+$ reference electrode and platinum mesh auxiliary electrode were used and measurements conducted in the propylene carbonate (TBA.PF$_6$) or ionic liquid electrolytes. Absorption spectra (250-1100 nm) were obtained using a Shimadzu Model UV-1601 spectrophotometer and polymer films grown galvanostatically (1 mA/cm² for 3 min) on indium-tin-oxide (ITO) coated glass.

Figure 9:
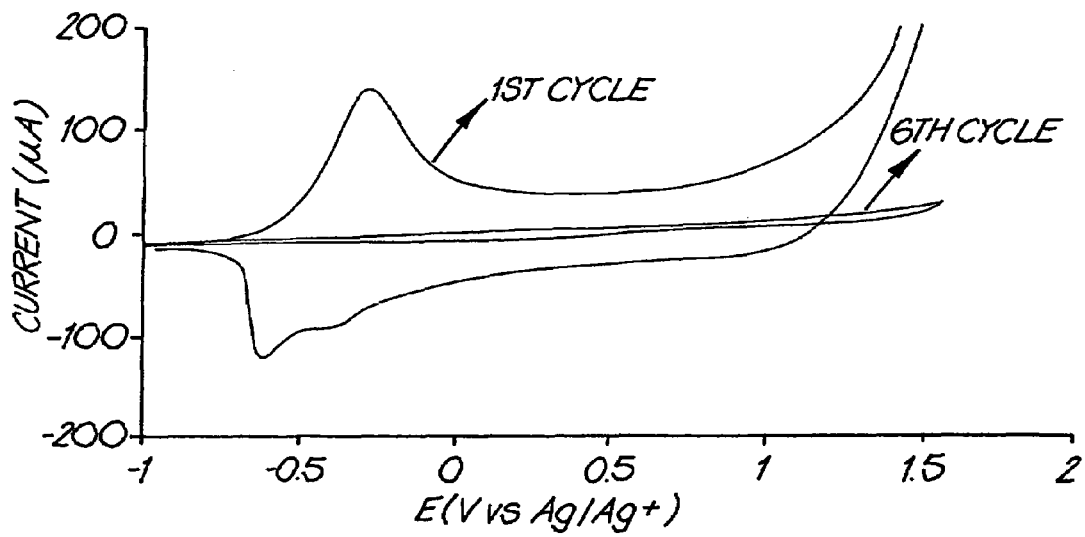
FIG. 9 is a cyclic voltammogram obtained using $PPy/PF_6$ coated platinum electrode in polypropylene carbonate (0.25M $TBA.PF_6$). Scan rate=100 mV/see.

Using the propylene carbonate containing TBA.PF$_6$ as electrolyte, degradation in the polymer electroactivity was observed if the anodic potential range was extended beyond +1.30 V. This degradation is attributed to the irreversible "over oxidation" previously observed for polypyrroles at anodic potentials where the polymer backbone becomes susceptible to attack from nucleophiles in the electrolyte. When the limit was extended to +1.55 V (FIG. 9) the breakdown was rapid and all electroactivity was lost after 6 potential cycles.

Figure 10:
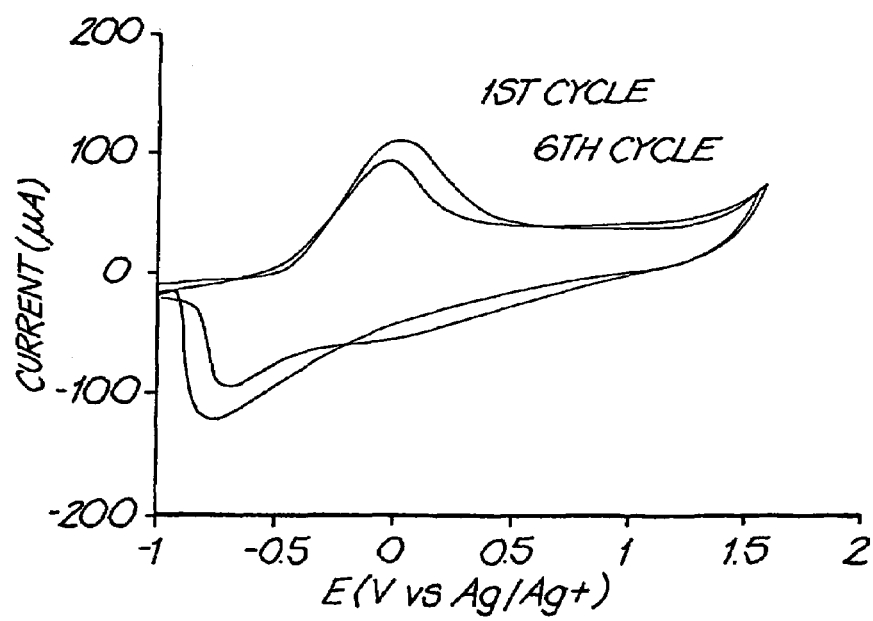
FIG. 10 is a cyclic voltammogram obtained using Ppy/$PF_6$ coated platinum electrode in 1-butyl-3-methylimidazolium hexaflourophosphate. Scan rate=100 mV/sec.
Figure 12:
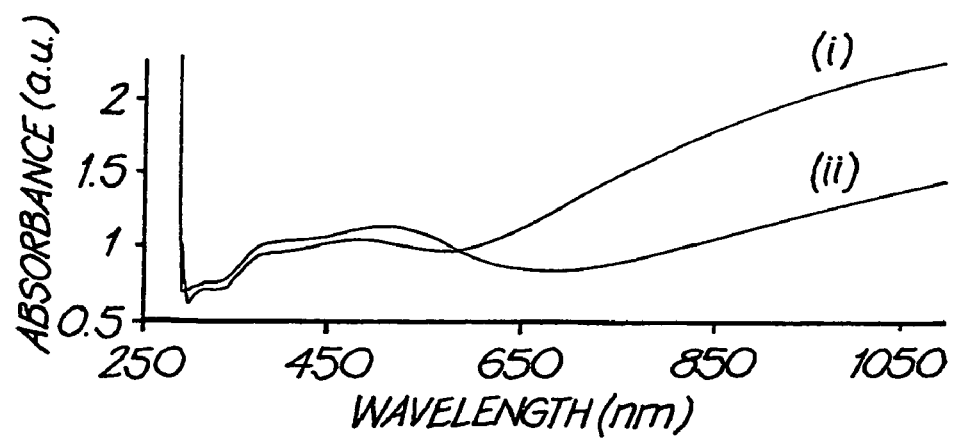
FIG. 12 is a UV-visible spectra of $Ppy/PF_6$ deposited galvanostatically (1 $mA/cm^2$ for 3 min) onto ITO coated glass (i) Polymer in the oxidised state, (ii) Oxidised polymer after CV in propylene carbonate (0.25M $TBA.PF_6$) solution for 6 cycles over the potential range: −1 V to +1.55 V. Scan rate=100 mV/sec.

When the polypyrrole was deposited on ITO glass and cycled over the same potential range the changes in the UV-visible spectra observed at long wavelengths FIG. 12) are related to a decreased absorption due to the bipolarons. The spectral changes are consistent with the nucleophilic attack reducing π-conjugation length and bipolaron activity. The loss of conjugation leads to reduced conductivity and electroactivity. When BMI.PF$_6$ (IL1) was used as the electrolyte no such degradation was observed over this same potential range (FIG. 10). The increased stability was confirmed when the experiment was repeated on PPy-coated ITO glass with no changes in the UV-visible spectra observed. In fact, using BMI.PF$_6$ the potential could be scanned to +1.75 V without any change in the cyclic voltammetry being observed.

Figure 11:
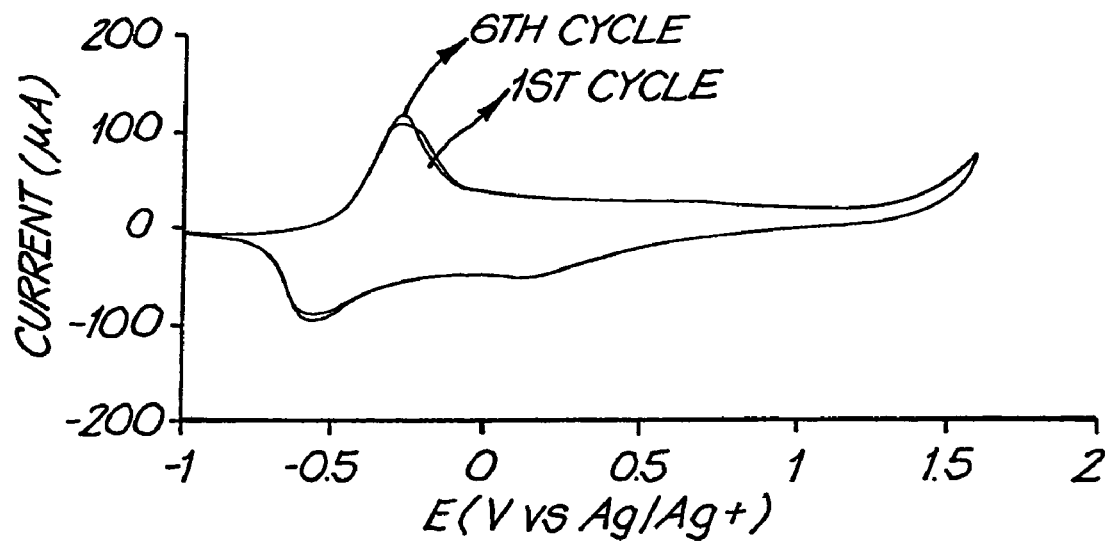
FIG. 11 is a cyclic voltammogram obtained using PPy/$PF_6$ coated platinum electrode in 1-ethylmethyl imidzolium bis(trifluoromethanesulfonyl) amide. Scan rate=100 mV/sec.

Similarly, in EMI.TFSA (FIG. 11) no degradation of electroactivity was observed with a +1.55 V potential limit. With this electrolyte the upper limit could be extended to +2.0 V without degradation being observed. Again, UV-visible spectra obtained for film deposited on ITO glass confirmed that no degradation occurred after cycling the potential to those extended anodic regions for 5 cycles. These results indicate a greater degree of polymer stability to potential cycling over extreme limits when these very electrochemically stable ionic liquid electrolytes are used

EXAMPLE 6

Actuation and displacement tests on an electromechanical actuator prepared as in Example 4 were carried out in each of the electrolytes utilised in Example 5 using two different test systems. The displacement test involved the use of a two electrode cantilever system as illustrated in FIG. 13. Briefly, the system comprises an electrolytic cell including a housing 12 in which the electromechanical actuator 14 is arranged. The platinum wire conductor of the actuator is secured at one end to a pin 16 that is slidable relative to the housing upon the application of a voltage to the actuator. The opposite end region of the conductor is clamped at the base of the housing and is connected to a power source. The housing contains a propylene carbonate electrolyte 18 with tertiary butylammonium hexafluorophosphate TBA.PF6 (0.1M) surrounds the conducting polymer of the actuator. A spring 20 is located between the housing and the head of the pin for simulating a load of 5.0 grams during actuation of the actuator. An auxiliary electrode located in the housing is indicated by the numeral 22. The cantilever 24 for indicating displacement achieved by the actuator is connected to the head of the pin.

The amount of displacement was measured from a video recording of the cantilever movement and the strain calculated according to the original length of the actuator. A repetitive pulse (500 mS duration) was applied over a number of potential ranges and the maximum strain as well as the average s rate over the 500 mS period determined. Specifically, 100 cycles were applied at each potential range selected starting with ±1 V and increasing to ±5 V. The strain data recorded were average values over the 500 mS period. The electrolytic efficiency was determined during these experiments from current flow. As expected, in all electrolytes the electrolytic efficiency, strain and strain rate increased with increasing magnitude of the applied potential (see for example Table 5).

TABLE 5

Effect of electrolyte used on electrolytic efficiency and strain obtained.

| Electrolyte Applied Potential (V) | PC (TBA.PF$_6$) | | IL 1 (BMI.PF$_6$) | | IL 2 (EMI.TFSA) | |
|---|---|---|---|---|---|---|
| | Electrolytic Efficiency (%) | Max Strain (%) | Electrolytic Efficiency (%) | Max Strain (%) | Electrolytic Efficiency (%) | Max Strain (%) |
| +/−1 | 9.38 | 0.36 | 5.31 | 0.22 | 0.47 | 0.01 |
| +/−2 | 18.3 | 0.45 | 12.08 | 0.32 | 7.31 | 0.2 |
| +/−3 | 37.8 | 0.64 | 20.25 | 0.54 | 15.83 | 0.3 |
| +/−4 | 51.36 | 0.90 | 42.70 | 0.90 | 34.62 | 0.7 |
| +/−5 | 56.28 | 1.00 | 56.60 | 1.35 | 51.02 | 1.53 |

At most potentials (all except ±5V) there is a higher electrolytic efficiency in propylene carbonate TBA.PF$_6$ electrolyte than either ionic liquid electrolyte, reflecting the higher ionic conductivity of the propylene carbonate electrolyte compared with the ionic liquids. Interestingly, at ±5V the electrolytic efficiencies observed are approximately the same (50-56%) in all electrolytes, yet there is significant differences in the % strain generated. In the ionic liquid electrolytes a higher strain is generated for a given charge passed when a large potential is applied. These different characteristics reflect fundamental differences in the actuation mechanism of PPy.PF$_6$ in ionic liquids compared with the propylene carbonate based electrolyte. The results may also be affected by Faradaic reactions occurring in the propylene carbonate electrolyte that do not contribute to actuation but still consume charge.

The actuator was then cycled over several thousand cycles using propylene carbonate (TBA.PF$_6$) electrolyte. Each cycle involved application of ±5V (1 Hz). After 3,600 cycles the strain recorded decreased to 0.3% (FIG. 14). These experiments were then repeated in BMI.PF$_6$ (FIG. 14). The strain attainable over several thousand cycles was significantly more consistent in the ionic liquids reflecting the higher electrochemical stability of the PPy in these electrolytes.

Actuator strain data was obtained using a conventionally known beam balance arrangement[10] and stain versus applied potential was plotted. The expansion contraction of the polymer was recorded using a linear variable distance transducer when a ±2.5V triangle waveform with a potential scan rate of 50 mV/s was applied. For EMI.TFSA this experiment was repeated under different loads. The results are also illustrated in FIG. 14.

The direction of actuation was clearly shown to be reversed in the ionic liquids compared with the propylene carbonate based electrolyte (see FIG. 15). These results show that the movement of the ionic liquid cation in/out of the polymer at negative potentials is the dominant mechanism leading to actuation. Conversely, in the propylene carbonate electrolyte it is the anion (PF$_6^-$) that is induced to move into (positive potentials) and out of (negative potentials) the polymer. Even using the larger BMI molecule it is cation movement that predominates and the amount of strain (>3%) was increased compared with that observed (2.5%) using the EMI cation. For EMI.TFSA this experiment was repeated under load with the strain decreasing from 3.0% (no load) to 2.5% (6.5MPa stress applied) (see FIG. 16). A much higher decrease in strain was observed when a propylene carbonate based electrolyte was used from 2.5% (no load) to 0.5% at 2.5MPa.

Further evidence that the cation motion dominates the actuation mechanism can be observed from the contrast in the maximum strain obtained form the two ionic liquids under conditions of rapid testing (such as cycling shown in FIG. 14) as compared with a slower potential scan (FIG. 15). In the latter experiment, the BMI.PF$_6$ ionic liquid shows significantly larger strains at negative potentials as compared with EMI.TFSA and a greater positive potential is required to complete the charge/discharge cycle with the BMI containing system. Given the relative size of BMI and EMI, the latter is considerably smaller and may be incorporated more rapidly into the polypyrrole, whereas BMI ultimately shows a larger response (due to its larger size) but achieves this response more slowly. It is also noted the EMI.TFSA ionic liquid maintains a higher strain % than the other electrolyte systems. The TFSA containing electrolyte is inherently more environmentally stable than those containing the PF$_6^-$anion.

Another, unique, feature of actuation in ionic liquids compared to other electrolytes is the absence of osmotic effects. In ionic liquids there is no solvent present so osmosis does not occur. Interestingly, the strain amplitude, under equivalent conditions, is slightly higher for ionic liquid electrolytes (where osmosis is absent) compared with TBA.PF6 in propylene carbonate (where osmosis is expected).

From the above results, ionic liquids therefore provide an alternative electrolyte for electromechanical actuators. The wide electrochemical potential window provides an added degree of stability enabling many thousands of actuator cycles. In addition, an unexpected result has been obtained in terms of actuator mechanism where cation inclusion/expulsion predominates in determining the mode of actuation. The actuator performance in terms of strain under load and cycle life time, was significantly improved in the ionic liquid electrolytes compared with the conventional propylene carbonate based organic electrolyte used.

Although the present invention has been described hereinbefore with reference to a number of preferred embodiments, the skilled addressee will understand that numerous modifications and improvements are possible without departing from the scope of the invention.

The invention claimed is:

1. An electromechanical actuator for effecting a desired action, comprising:
   a conducting polymer and a conductor for conducting voltage along the polymer from one end region of the polymer to an opposite end region of the polymer;
   wherein the conductor is arranged in a concertina pattern along the polymer for extension and retraction with expansion and contraction of the polymer, and extends along the polymer from the one end region to the opposite end region.

2. An electromechanical actuator according to claim 1 wherein the conductor is in intimate electrical contact along the polymer from the one end region of the polymer to the opposite end region.

3. An electromechanical actuator according to claim 1 wherein the conductor is embedded in the polymer.

4. An electromechanical actuator according to claim 1 wherein the conductor is wound in a helix along the polymer for conducting the voltage along the polymer from one end region of the polymer to the opposite end region.

5. An electromechanical actuator according to claim 1 further comprising a template received by the polymer and wherein the polymer is slidable along the template with expansion and contraction of the polymer.

6. An electromechanical actuator according to claim 5 wherein one end region of the conductor is in electrical contact with one end region of the template and an opposite end region of the conductor is in electrical contact with a corresponding end region of the template.

7. An electromechanical actuator according to claim 5 wherein the template comprises a further conductor.

8. An electromechanical actuator according to claim 1 wherein the conducting polymer is in the form of a tube.

9. An electromechanical actuator according to claim 1 further comprising an electrical connector for facilitating connection of the conductor to an electrical circuit and being connected to one end region of the conductor.

10. An electromechanical actuator according to claim 9 comprising a further electrical connector for facilitating connection of the conductor to the electrical circuit and being connected to an opposite end region of the conductor.

11. An electromechanical actuator according to claim 1 wherein the polymer is selected from the group consisting of polyaniline, polypyrrole, polythiophene, derivatives thereof, and mixtures of the foregoing.

12. An electromechanical actuator according to claim 11 wherein the derivatives are selected from the group consisting of alkyl, alkoxy, amine and alcohol derivatives.

13. An electromechanical actuator according to claim 1 wherein the conductor is a wire.

14. An electromechanical actuator for effecting a desired action, comprising:
    an outer actuator comprising a tubular conducting polymer having a hollow interior;
    an inner actuator comprising a further conducting polymer; and
    an electrolyte in a space defined between the& inner actuator and the outer actuator;
    wherein the inner actuator is arranged within the outer actuator and lies along the hollow interior of the outer actuator for axial expansion and contraction within the outer actuator.

15. An electromechanical actuator according to claim 14 wherein the inner actuator is arranged within the outer actuator for axial expansion and contraction of the further polymer with axial expansion or contraction of the tubular conducting polymer.

16. An electromechanical actuator according to claim 14 wherein the inner actuator is arranged within the outer actuator for axial expansion and contraction in opposition to axial expansion and contraction of tubular conducting polymer.

17. An electromechanical actuator according to claim 14 wherein at least one of the inner actuator and the outer actuator further comprises a conductor for conducting voltage along either the further polymer or the tubular conducting polymer of the actuator to which the conductor corresponds from one end region thereof to an opposite end region thereof, and wherein the conductor is adapted for axially extending and retracting.

18. An electromechanical actuator according to claim 17 wherein the inner actuator incorporates a said conductor for conducting voltage along the further polymer from one end region of the further polymer to an opposite end region of the further polymer, and wherein the conductor is adapted for axially extending and retracting with the axial expansion and contraction of the further polymer.

19. An electromechanical actuator according to claim 18 wherein the conductor is in intimate electrical contact along the further polymer from the one end region to the opposite end region.

20. An electromechanical actuator according to claim 18 wherein the conductor is embedded in the further polymer.

21. An electromechanical actuator according to claim 18 wherein the conductor is wound in a helix along the further polymer for conducting the voltage along the further polymer form the one end region of the polymer to the opposite end region.

22. An electromechanical actuator according to claim 14 wherein the further conducting polymer is in tubular form.

23. An electromechanical actuator according to claim 14 wherein the tubular conducting polymer and the further conducting polymer are the same or different.

24. An electromechanical actuator according to claim 23 wherein the further conducting polymer is selected from the group consisting of polyaniline, polypyrrole, polythiophene, derivatives thereof, and mixtures of the foregoing.

25. An electromechanical actuator according to claim 14 wherein the electrolyte is an ionic liquid electrolyte.

26. An electromechanical actuator according to claim 25 wherein the ionic liquid electrolyte comprises an ionic liquid selected from the group consisting of 1-ethyl-3-methyl imidazolium bis(trisfluoromethanesulfonyl) amide and 1-butyl-3-methylimidazolium hexafluorophosphate.

* * * * *

UNITED STATES PATENT AND TRADEMARK OFFICE
CERTIFICATE OF CORRECTION

PATENT NO. : 7,242,134 B2
APPLICATION NO. : 10/496262
DATED : July 10, 2007
INVENTOR(S) : Gordon G. Wallace et al.

It is certified that error appears in the above-identified patent and that said Letters Patent is hereby corrected as shown below:

On The Title Page,

Item (57), line 2, "conducing" should be -- conducting --.

At Column 20, line 1, "the&" should be -- the --.

At Column 20, line 41, "form" should be -- from --.

Signed and Sealed this

Tenth Day of June, 2008

JON W. DUDAS
*Director of the United States Patent and Trademark Office*